United States Patent
Matsumoto et al.

[11] Patent Number: 5,110,645
[45] Date of Patent: May 5, 1992

[54] SHEATH OF ARTICULATED TUBE FOR ENDOSCOPE

[75] Inventors: Jun Matsumoto; Ryouchi Tanaka, both of Hachioji, Japan

[73] Assignee: Olympus Optical Company Ltd., Japan

[21] Appl. No.: 764,043

[22] Filed: Sep. 2, 1991

Related U.S. Application Data

[63] Continuation of Ser. No. 102,049, Sep. 29, 1987, abandoned.

Foreign Application Priority Data

Oct. 3, 1986 [JP] Japan .................. 61-235747

[51] Int. Cl.$^5$ .................. F16L 11/18; C08L 27/18
[52] U.S. Cl. .................. 428/36.9; 264/331.13; 264/331.14; 264/236; 524/520
[58] Field of Search .................. 428/36.9; 524/520; 264/331.13, 331.14, 347, 236

[56] References Cited

U.S. PATENT DOCUMENTS

| | | | |
|---|---|---|---|
| 2,789,960 | 4/1957 | Smith | 524/520 |
| 2,975,785 | 3/1961 | Sheldon | 128/6 |
| 3,071,161 | 1/1963 | Ulrich | 138/120 |
| 3,162,214 | 12/1964 | Bazinet | 138/120 |
| 4,396,744 | 8/1983 | Close | 524/520 |
| 4,595,720 | 6/1986 | Stivers et al. | 524/520 |

Primary Examiner—James J. Seidleck
Attorney, Agent, or Firm—Ostrolenk, Faber, Gerb & Soffen

[57] ABSTRACT

A sheath of an articulated tube for an endoscope is formed of material produced by adding polymer of fluorine-contained rubber material of triple copolymer of vinylidene fluoride-hexafluoropropylene-tetrafloroethylene as a main component, heat-proof plasticizer of binary copolymer of vinylidene fluoride-hexafluoropropyelne for reducing hardness, MT carbon filler, Perhexa 25B of peroxide vulcanizing agent and triallyl isocyanurate (TAIC) as peroxide vulcanizing assistant, resulting in reduced hardness, good operability while bending, good drug-, heat-, and sterilization-proof and long durability.

6 Claims, 1 Drawing Sheet

SHEATH OF ARTICULATED TUBE FOR ENDOSCOPE

This is a continuation of application Ser. No. 07/102,049 filed on Sep. 29, 1987 is now abandoned.

BACKGROUND OF THE INVENTION

The present invention relates to a sheath of an articulated tube for endoscopes.

In an endoscope, which is used for observing and treating various affections by inserting into a colon of a human body, an articulated tube thereof is particularly required not to become fatigued even when being repeatedly subjected to expansion and contraction by bending the articulated tube. For this reason, it is desirable for a sheath of the articulated tube to have hardness as low as possible and a good recoverable nature of deformation and to have no effect upon operability thereof by the tensile strength while bending. In other words, the sheath requires a reduced modulus of elasticity and a reduced permanent set. In addition, the sheath requires an absence harmful substances so that there is no possibility of harmful substances being extracted into a colon and, when an endoscope is pulled out from a colon and subjected to cleaning, disinfection and the like, not to be affected by an antiseptic solution and the like. To meet these conditions, substances such as ethylene-propylene rubber (EP Rubber) and nitryl-butadiene rubber (NBR) have been used as a sheath. These substances have practically met such conditions as having a reduced hardness, modulus of elasticity and permanent set, no possibility of harmful substances being extracted from rubber materials and an injurious effect on a human body.

These substances, however, have the disadvantage that they crumble and decay in a sterilizing operation with ethylene oxide gas. Specifically, in an autoclave method under the conditions in high temperature of 132° C. and high pressure of 2.3 kg/cm² vapor, these substances deteriorate, losing their initial properties, have their tensile strength reduced due to hardening of rubber matter, tear by elongation and shrinkage caused by bending, increase in permanent set, reversely, due to softening of rubber matter to cause wrinkles and become thick in diameter at bent portions, thereby causing pain to a patient during insertion of an endoscope. As a rubber material withstanding to the autoclave process, however, fluorine-contained rubber is available but does not meet the conditions of reduced hardness, modulus of elasticity and the like as required on a sheath of an articulated tube for use in an endoscope.

A further trouble in EP Rubber and NBR materials which have been used is that swelling may result from immersing them in an antiseptic solution of Isodine (trademark name) for a long term. A comparison between EP Rubber and fluorine-contained rubber as a conventional sheath material is shown in Table 1.

TABLE 1

|  |  |  | EP Rubber | Fluorine-contained rubber |
|---|---|---|---|---|
| Hardness | Hs |  | 45 | 60 |
| Tensile strength | TB | (kg/cm²) | 100 | 75 |
| Elongation | EB | (%) | 700 | 250 |
| Tearing strength | TR | (kg/cm) | 22.0 | 25 |
| 100% Tensile stress | M | 100% | 9.5 | 14 |
| Permanent set | P.S. |  | 15 | 17 |

TABLE 1-continued

|  |  | EP Rubber | Fluorine-contained rubber |
|---|---|---|---|
| After an autoclave method has been applied to 300 examples | Hardness | 50 | 60 |
|  | Tensile strength | 75 | 78 |
|  | Elongation | 350 | 230 |
|  | Tearing strength | 10 | 25 |
|  | 100% Tensile stress | 14.5 | 15 |
|  | Permanent set | 17 | 17 |
| Notification No. 301 of the Japanese Ministry of Health and Welfare |  | Accepted | Accepted |
| Immersion test in antiseptic solution of Isodine for one month |  | Swelled | No swelling |
| Mounting test on endoscope |  | Operability Good | Operability Poor |

In Table 1, after the autoclave method has been applied to 300 examples, EP Rubber develops a tendency to extremely increase hardness and 100% tensile stress, whereas fluorine-contained rubber undergoes almost no change. In addition, it is found that regarding the immersion test in antiseptic solution of Isodine for one month, EP Rubber swells and fluorine-contained rubber does not swell. Fluorine-contained rubber, however, has an increased hardness and 100% modulus of elasticity, so that its operability is inferior to EP Rubber.

SUMMARY OF THE INVENTION

It is, accordingly, an object of the present invention to provide a sheath of articulated tube for use in an endoscope which has reduced hardness, modulus of elasticity and permanent set, no possibility of harmful substances being extracted, an excellent drug-proof nature without swelling or deterioration in antiseptic solutions and good bending operability with sterilization-proof and heat-proof properties.

According to the present invention, a sheath of articulated tube for use in an endoscope is formed of material produced by adding polymer of fluorine-contained rubber material of triple copolymer of vinylidene fluoride-hexafluoropropylene-tetrafluoroethylene as a main component, heat-proof plasticizer of binary copolymer of vinyldene fluoride-hexafluoropropylene for reducing hardness, filler of MT carbon (medium thermal furnace black), Perhexa 25B peroxide vulcanizing agent (2,5-dimethyl-2,5-di(t-butylperoxy)hexane), and triallyl isocyanurate (TAIC) of vulcanizing assistant.

Using such material, it is possible to obtain a sheath of articulated tubes having a reduced hardness, being operability while bending and good drug-, heat- and sterilization-proof and long durability, for use in endoscopes.

DETAILED DESCRIPTION OF PREFERRED EMBODIMENT

Figure 1:
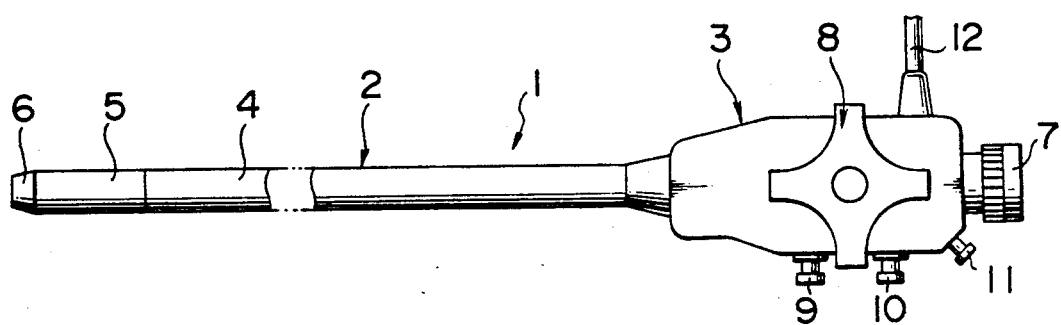
FIG. 1 is a general view of an endoscope.

In FIG. 1, an endoscope 1 comprises an insertable portion 2 and an operating portion 3. The insertable portion 2 is connected through a flexible tube portion 4 and an articulated tube portion 5 to a distal end portion 6. The operating portion 3 includes an eyepiece assembly 7 for observing an affected part in a colon, an operating knob 8 for remotely operating the articulated tube portion 5 to bend right and left and up and down, a button 9 for supplying air and water, a button 10 for suction and an inlet 11 for forceps. Operating portion 3 is also provided with a light guide cable 12 which is to be connected to a light source (not shown).

Figure 2:
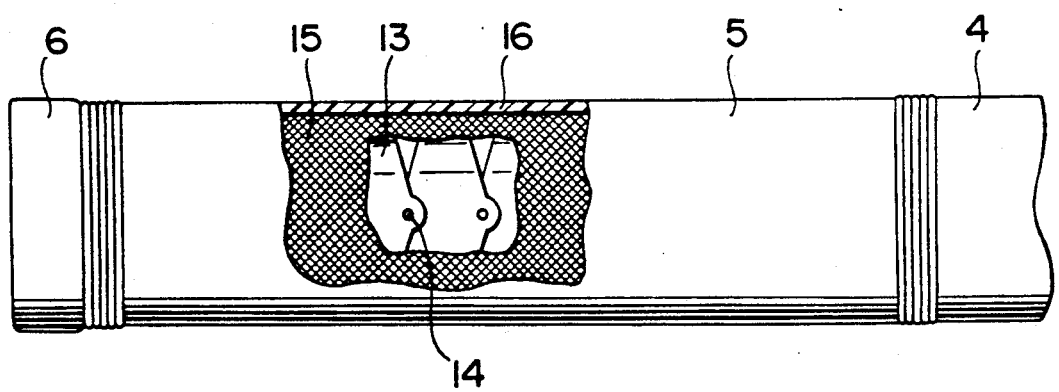
FIG. 2 is an enlarged side and partly broken view of an articulated tube for an endoscope.

The articulated tube portion 5 of the insertable portion 2, as shown in FIG. 2, is formed by a plurality of articulated tubes 13 which are connected to each other by a pin 14 so as to be bendable within a colon. Although not shown, two or four wires pass through the articulated tubes 13 and are connected to operating knob 8 on the operating portion 3 such that the articulated tubes 13 can be bent in a desired direction by rotating the operating knob 8. A reticular tube 15, formed by knitting fine metal wires, is covered on the outer periphery of the articulated tubes 13. A sheath 16 which covers the outer periphery of the reticular tube 15, extends from the distal end portion 6 through the articulated tube portion 5 to the flexible tube portion 4. The sheath 16 is made of compounds shown in the following example.

EXAMPLE

Triple-copolymer of vinylidene fluoride-hexafluoropropylene-tetrafluoroethylene (a trademark name: Daikin G 902), of 100 parts, Perhexa 25B of 0.5 part as a peroxide vulcanizing agent and triallyl isocyanurate (TAIC), 1.5 parts, as a peroxide vulcanizing assistant, MT carbon 10 parts, as a filler and a binary copolymer of vinylidene fluoride-hexafluoropropylene (a trademark name: Daikin G 101 or a trademark name: Viton LM), 10 parts, as a plasticizer were mixed and dispersed by two rolls. Subsequently, they were molded by applying compression with a hot press at a temperature of 160° C. for 10 minute and subjected to secondary vulcanization by hot blast at a temperature of 180° C. for four hours. Thus, sheath 16 was manufactured and a 2 mm thick sheet for an experimental test was manufactured at the same time. The resulting data are shown in Table 2.

TABLE 2

| Hardness | Hs | | 53 |
|---|---|---|---|
| Tensile strength | TB | | 100 |
| Elongation | EB | | 500 |
| Tearing strength | TR | | 21.0 |
| 100% Tensile stress | M | 100% | 11.0 |
| Permanent set | P.S. | | 13 |
| After an | Hardness | | 53 |
| autoclave | Tensile strength | | 99 |
| method | Elongation | | 490 |
| is | Tearing strength | | 20.0 |
| applied | 100% Tensile stress M 100% | | 11.0 |
| to 300 | Permanent set | | 13 |
| examples | | | |
| Notification No. 301 of the Japanese Ministry of Health and Welfare | | | Accepted |
| Immersion test in antiseptic solution of Isodine for one month | | | No swelling |
| Mounting test on an endoscope | | | Operability |

TABLE 2-continued

| | Good |
|---|---|

As seen from the test data, it is possible to manufacture a sheath of articulated tubes to satisfactorily meet the following conditions by adding heat-proof plasticizer to fluorine group elastomer and further adding carbon filler, peroxide vulcanizing agent and peroxide vulcanizing assistant of peroxide to them.

(1) Reduced hardness, modulus of elasticity and permanent set,
(2) No possibility of harmful substances being extracted,
(3) No swelling and deterioration in an antiseptic solution, and
(4) No deteriorative softening or hardening caused by a sterilization process.

What is claimed is:

1. A sheath of an articulated tube for use in an endoscope, comprising:
    a terpolymer of vinylidene fluoride-hexafluoropropylene-tetrafluoroethylene as a main component;
    a copolymer of vinylidene fluoride-hexafluoropropylene as a heat-proof plasticizer;
    medium thermal furnace black as a filler; and
    a peroxide vulcanizing agent and a peroxide vulcanizing assistant.

2. A sheath according to claim 1, which comprises 100 parts of the terpolymer of vinylidene fluoride-hexafluoropropylene-tetrafluoroethylene, 5 through 20 parts of the copolymer of vinylidene fluoride-hexafluoropropylene, 5 through 20 parts of medium thermal furnace black, 0.1 through 1 part of 2,5-dimethyl-2,5-di(t-butylperoxy)hexane and 0.1 through 2 parts of triallyl isocyanurate.

3. A sheath according to claim 2 in which the amount of copolymer is 10 parts, the amount of medium thermal furnace black is 10 parts, the amount of peroxide is 0.5 part and the amount of triallyl isocyanurate is 1.5 parts.

4. A method of making a sheath of an articulated tube for use in an endoscope which comprises mixing and dispersing a terpolymer of vinylidene fluoride-hexafluoropropylene-tetrafluoroethylene as a main component, a copolymer of vinylidene fluoride-hexafluoropropylene as a heat-proof plasticizer, medium thermal furnace black as a filler, a peroxide vulcanizing agent and a peroxide vulcanizing assistant with a two roll mill, molding the mixed and dispersed composition by applying compression with a hot press at a temperature of 160° C. for 10 minutes and subjecting the molded mixture to secondary vulcanization by hot blast at a temperature of 180° C. for four hours.

5. The method of claim 4 in which the materials mixed contain per 100 parts of the terpolymer, 5-20 parts of the copolymer, 5-20 parts of the medium thermal furnace black, 0.1-1 part of 2,5-dimethyl-2,5-di(t-butylperoxy) hexane and 0.1-2 parts of triallyl isocyanurate.

6. The method of claim 5 in which the amount of copolymer is 10 parts, the amount of medium thermal furnace black is 10 parts, the amount of peroxide is 0.5 part and the amount of triallyl isocyanurate is 1.5 parts.

* * * * *

UNITED STATES PATENT AND TRADEMARK OFFICE
CERTIFICATE OF CORRECTION

PATENT NO. : 5,110,645
DATED : May 5, 1992
INVENTOR(S) : Jun Matsumoto et al.

It is certified that error appears in the above-identified patent and that said Letters Patent is hereby corrected as shown below:

On the title page, Item --[75] Inventors: for "Ryouchi" read --Ryouichi--.

In the Abstract, line 4, for "tetrafloro" read -- tetrafluoro- --; line 7, for "propyelne" read --propylene--; and line 8, for "of" read --as--.

Column 3, line 30, for "carbon" read --carbon,--.

Signed and Sealed this

Twenty-fourth Day of August, 1993

Attest:

BRUCE LEHMAN

Attesting Officer    Commissioner of Patents and Trademarks